US008302494B2

(12) United States Patent
Han et al.

(10) Patent No.: US 8,302,494 B2
(45) Date of Patent: Nov. 6, 2012

(54) SENSOR FOR QUANTITATIVE MEASUREMENT OF ELECTROMECHANICAL PROPERTIES AND MICROSTRUCTURE OF NANO-MATERIALS AND METHOD FOR MAKING THE SAME

(75) Inventors: Xiaodong Han, Beijing (CN); Pan Liu, Beijing (CN); Yonghai Yue, Beijing (CN); Ze Zhang, Beijing (CN)

(73) Assignee: Beijing University of Technology, Beijing (CN)

( * ) Notice: Subject to any disclaimer, the term of this patent is extended or adjusted under 35 U.S.C. 154(b) by 365 days.

(21) Appl. No.: 12/756,131

(22) Filed: Apr. 7, 2010

(65) Prior Publication Data

US 2011/0107472 A1 May 5, 2011

(30) Foreign Application Priority Data

Oct. 30, 2009 (CN) .......................... 2009 1 0209434

(51) Int. Cl.
*G01L 1/18* (2006.01)
(52) U.S. Cl. .................... 73/862.634; 977/852
(58) Field of Classification Search ............ 73/775, 73/776, 778, 788, 789, 790, 808, 811, 856, 73/860, 864.634; 977/852, 880, 881
See application file for complete search history.

(56) References Cited

U.S. PATENT DOCUMENTS

| | | | | |
|---|---|---|---|---|
| 5,959,200 A | * | 9/1999 | Chui et al. ........................ | 73/812 |
| 6,817,255 B2 | * | 11/2004 | Haque et al. ............. | 73/862.638 |
| 7,586,105 B2 | * | 9/2009 | Molhave ......................... | 73/856 |
| 7,752,916 B2 | * | 7/2010 | Han et al. ......................... | 73/789 |
| 7,762,146 B2 | * | 7/2010 | Brodland ......................... | 73/856 |
| 7,827,660 B2 | * | 11/2010 | Gogoi et al. .................. | 29/25.35 |
| 8,069,733 B2 | * | 12/2011 | Han et al. ......................... | 73/781 |
| 2005/0034542 A1 | * | 2/2005 | Thaysen .................. | 73/862.634 |
| 2009/0194689 A1 | * | 8/2009 | Abramson et al. ............ | 250/307 |

OTHER PUBLICATIONS

M. A. Hague and M. T. A. Saif, "Deformation mechanisms in free-standing nanoscale thin films—A quantitative in situ transmission electron microscope study" Proceedings of the National Academy of Sciences, vol. 101, p. 6335, 2004.

(Continued)

*Primary Examiner* — Lisa Caputo
*Assistant Examiner* — Punam Roy
(74) *Attorney, Agent, or Firm* — J.C. Patents

(57) ABSTRACT

A sensor for quantitative testing electromechanical properties and microstructure of nano-materials and a manufacturing method for the sensor are provided. The sensor comprises a suspended structure, pressure-sensitive resistor cantilevers, support beams, bimetallic strip and other components. When the bimetallic strip produces bending deformation, one of the pressure-sensitive resistor cantilevers is actuated and then stretches the low-dimensional nano-materials which drive the other pressure-sensitive resistor cantilever to bend. Through signal changes are outputted by the Wheatstone bridge, the variable stresses of low-dimensional nano-materials are obtained. Meanwhile, the variable strains of low-dimensional nano-materials are obtained by the horizontal displacements between two cantilevers, so the stress-strain curves of low-dimensional nano-materials are worked out. When the low-dimensional nano-materials are measured in the power state, the voltage-current curves are also obtained. In addition, by the help of high resolution imaging system in the transmission electron microscopy, the mechanical-electrical-microstructure relationship of the nano-materials can be recorded in situ and in atomic lattice resolution.

2 Claims, 7 Drawing Sheets

OTHER PUBLICATIONS

Yong Zhu and Horacio D. Espinosa, "An electromechanical material testing system for in situ electron microscopy and applications", Proceedings of the National Academy of Sciences, vol. 102, p. 14503-14508, 2005.

XiaoDong Han, Kun Zheng, YueFei Zhang, XiaoNa Zhang, and Ze Zhang, "Low Temperature In-Situ Large-Strain-Plasticity of Silicon Nanowires", Advanced Materials, 2007,19,2112.

YueFei Zhang, XiaoDong Han, Kun Zheng, XiaoNa Zhang, and Ze Zhang, "Direct observation of super-plasticity of beta-SiC nanowires at low temperature", Advanced Functional Materials, 2007.17, 3435-3440.

T. Chu Duc, J. F. Creemer, and Pasqualina M. Sarro, "Piezoresistive Cantilever Beam for Force Sensingin Two Dimensions", IEEE Sensors Journal, vol. 7, No. 1, 2007.

J.Y. Huang, S. Chen, S. H. Jo, Z. Wang, D. X. Han, G. Chen, M. S. Dresselhaus, and Z. F. Ren, "Atomic-Scale Imaging of Wall-by-Wall Breakdown and Concurrent Transport Measurements in Multiwall Carbon Nanotubes", Physics review letters, vol. 94, 236802, 2005.

* cited by examiner

SENSOR FOR QUANTITATIVE MEASUREMENT OF ELECTROMECHANICAL PROPERTIES AND MICROSTRUCTURE OF NANO-MATERIALS AND METHOD FOR MAKING THE SAME

CROSS-REFERENCE TO RELATED APPLICATIONS

This application claims the priority benefits of China application No. 200910209434.1 filed on Oct. 30, 2009. The contents of China application No. 200910209434.1 are herein incorporated by reference in its entirety.

TECHNICAL FIELD OF THE INVENTION

The present invention relates to a sensor for measuring electro-mechanical properties of low-dimensional nano-materials by in situ high resolution transmission electron microscope (TEM), and a method for producing the sensor. More specifically, the present invention pertains to a TEM sample support or grid that allows the dynamic and real-time measure of the mechanical-electrical-microstructural relationships of individual nanostructure under stress field by in situ TEM at atomic lattice resolution level.

BACKGROUND OF THE INVENTION

As the basic building blocks of the micro- or nano-devices, nano-scale materials carry the information transport, storage and other important functions. The interest in the trend to reduce the dimensions of these devices in the semiconductor and information industries has given rise to a necessity for developing techniques for studying microstructure and the size effects on the mechanical strength and charge transport properties of individual functional nanostructure under external stress field and electric field. It is of great significance to the function of various units, storage density, efficiency, reliability and practical application of the devices.

Transmission electron microscopy (TEM) is a powerful tool for characterizing the micro-structures of solid state materials in the field of nano-science and nano-technology. In situ TEM experiments provide direct visualization and description of the events as they happen and give qualitative information about the structure-property-processing relationships. These knowledge are vital not only to the design and functional the nano-devices but also to the reliability and service. TEM grid is used to support the detected samples, which is usually Cu grid 3 mm in diameter with thin carbon film coatings. But at present the TEM grid is effective only for the static testing, and not for in situ manipulation and dynamic quantitative testing the properties of nano-material at the nano-scale even to atomic scale level.

Several approaches have been studied for in situ TEM manipulating, in order to quantitatively measure and image the structure-property relationships of individual nanostructure. See M. A. Hague and M. T. A. Saif, "Deformation mechanisms in free-standing nanoscale thin films—A quantitative in situ transmission electron microscope study" Proceedings of the National Academy of Sciences, Vol. 101, p. 6335, 2004; J. Y. Huang, S. Chen, S. H. Jo, Z. Wang, D. X. Han, G. Chen, M. S. Dresselhaus, and Z. F. Ren, "Atomic-Scale Imaging of Wall-by-Wall Breakdown and Concurrent Transport Measurements in Multiwall Carbon Nanotubes", Physics review letters, Vol. 94, 236802, 2005; and Yong Zhu and Horacio D. Espinosa, "An electromechanical material testing system for in situ electron microscopy and applications", Proceedings of the National Academy of Sciences, Vol. 102, p. 14503-14508, 2005. These methods integrated the micro-electromechanical systems (MEMS) unit with the TEM holder, thereby enabling simultaneous TEM observation and mechanical measurements, for investigating the relationship between nano-scale microstructure and interaction of individual nanostructure. But installing these devices inside the TEM holder that causes the holder can tilt a small angle and only a single axis tilting because of the narrow pole-piece gap. However, atomic-scale lattice resolution of a crystal is only achieved when a low-indexed zone axis of a crystal is precisely aligned parallel to the electron beam. This condition is difficult to fulfill in these in situ measuring systems that are subjected to mechanical manipulation influence during the experiments. Otherwise, the strain quantitation which reflects to mechanical property of nano-material calculating from the in situ high resolution TEM images present large error derived from artificial measuring process.

In recent years, accompany with development of science and technology, cantilever beam technology has been widely used in biology, physics, chemistry, materials, microelectronics and other research fields. These cantilever sensors obtained via lithography, etching and other processes on silicon-based material can be achieved high sensitivity, and the signal to noise ratio of the sensors are also very low, such as: IEEE Sensors Journal, Vol. 7, No. 1, 2007. However, it is difficult to integrate these sensors into the transmission electron microscope for real-time observation of microstructure, because of its large size, as well as the device that contains complex optical measurement systems which are applied to obtain displacement of cantilevers.

SUMMARY OF THE INVENTION

The present invention provides a sensor and a production method that overcomes the aforementioned limitations and fills the aforementioned needs by providing a method and TEM sample support or grid for measuring the electro-mechanical-property relationships of individual nanostructure by in situ high resolution TEM dynamic observation.

1. The present invention has unique structural design of the TEM sample grid that is movable with two thermal bimetallic strips which realize the plane tensile or compressive deformation of individual low-dimensional nano-materials in situ TEM. It is an object of the invention to provide a sample grid for high resolution electron microscopy which can be installed in the commercial heating holder such as JEOL 2010F. The grid with one movable thermal bimetallic strip can achieve dynamic observation processes by current heating the thermal bimetallic strip. The grid can fulfill the large tilt angle of X/Y-axial when in situ experiments are conducted which realize the dynamic sequential atomic resolution images.

2. The present invention provides a unique design method base on the Wheatstone bridge, which can translate lateral force signal into the output electrical signal changes. So that, the size of force changes about low-dimensional nano-materials can be outputted in situ and real-time.

3. The present invention utilizes the lithography technique and etching process in order to obtain two pressure-sensitive resistor cantilevers which have high accuracy. According to two cantilever displacement sensor signals, the stress and strain of low-dimensional nano-materials to draw the stress-strain curve can be obtained in situ and real-time, so as to carry out in situ mechanical properties measurement of nano-material. Meanwhile, the strain quantities of the low-dimensional nano-materials are available, while the corresponding electric signals measurement can be obtained, so that the electrical performance testing can also be conducted under specific stain state.

4. The present invention provides a conversion method of compression-stretching mode, which achieves changing compression suspended structure into tensile low-dimensional nano-materials, obviating the influence of bimetallic strip and nano-materials with direct contact. In that case, the smooth surface can be obtained and the factors such as heat conduction intrusion from bimetallic strip can be excluded. Temporality, the deformation process of low-dimensional nano-materials fulfils completely on the cantilever and suspended structures far away from the bimetallic strip.

According to the illustrative embodiments, demonstrating features and advantages of the present invention, the present invention provides a sample testing sensor which comprises a suspended structure, two same pressure-resistor cantilever beams, two support beams, conductive circuitries, and a driving bimetallic strip for in situ TEM experiments. The fabricated nano-material can be adhibited onto suspended structure and pressure-resistor cantilever beam. The bimetallic strip is movable when adding current flow into the heating resistors which are fabricated on the bimetallic strip. The fixed nano-material can be deformed accompanying with the moving of bimetallic strips. The mechanical property such as stress-strain relationship can be investigated by in situ TEM experiments. At the same time, leading two electrodes out of the sensor, the electric property of individual nano-material can be measured in situ under corresponding strain. Meanwhile, the dynamic structure evolution process of the nano-materials can be real-time recorded by in situ high resolution TEM at atomic sale. So, the present invention can provide the measurement of electromechanical properties of nano-materials and corresponding dynamic structure evolution.

Other objects, features and advantages of present invention will become clear through the following detailed description thereof taken in conjunction with the drawings.

BRIEF DESCRIPTION OF THE DRAWINGS

The features and advantage of the present invention will be apparent from the following detailed descriptions of the preferred aspects of the invention in conjunction with the accompanying drawings wherein.

Figure 1:
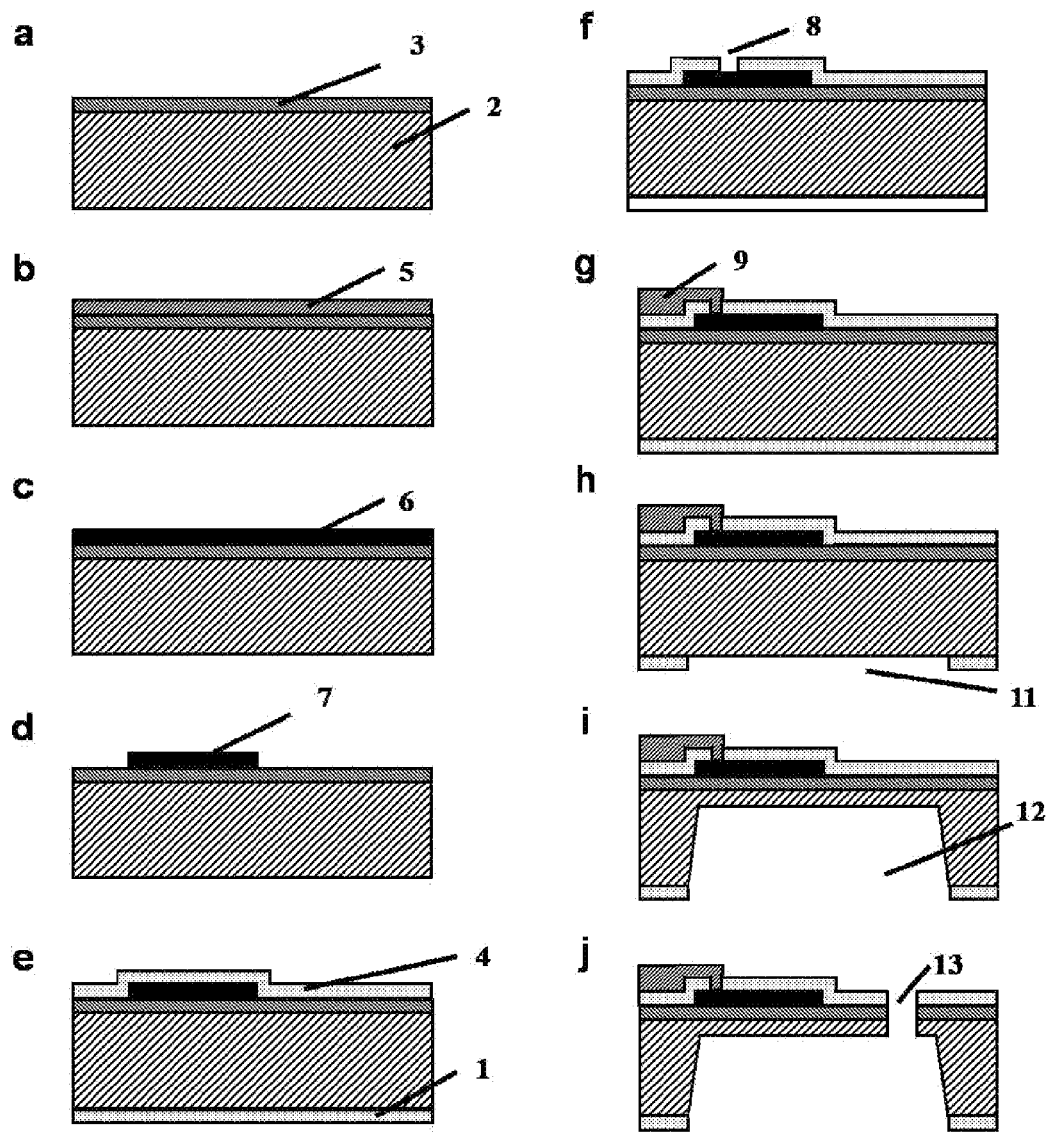
FIGS. 1a-1j illustrate production flow chart of the sensor of the present invention.

LIST OF PARTS SHOWN IN THE DRAWINGS 1, barrier layer; 2, silicon substrate; 3, epitaxial layer α; 4, insulating layer; 5, epitaxial layer β; 6, pressure-sensitive resistor layer; 7, pressure-sensitive resistor 8, contact holes; 9, electrodes; 10, metal wires; 11, windows; 12, silicon cup; 13, bilge holes; 14, bimetallic strip; 15, low-dimensional nano-materials; 16; suspended structure; 17, pressure-sensitive resistor cantilever beam α; 18, pressure-sensitive resistor cantilever beam 13; 19, support beams; 20, heat resistances; 21, thermocouple; 22, grooves

DETAILED DESCRIPTION OF THE INVENTION

The making and using of various embodiments of the present invention are discussed in detail below with accompanying drawings. It should be appreciated that the present invention provides many applicable inventive concepts that may be embodied in a wide various specific contexts. The sensor is used for quantitative measurement of the electromechanical properties and microstructure of the low-dimensional materials.

The specific structure of the sensor is shown in FIG. 1-FIG. 6. The sensor for quantitative measurement of the electromechanical properties and microstructure of the low-dimensional materials from the bottom up are as follows: a barrier layer (1), silicon substrate (2), epitaxial layer α (3), epitaxial layer β (5) grown on the epitaxial layers α (3). After doping epitaxial layer β (5), a pressure-sensitive resistor layer (6) is formed. Eight pressure-sensitive resistors (7) are etched and formed on the pressure-sensitive resistor layer (6). There are two variable pressure-sensitive resistors R1 and R2 located above the pressure-sensitive resistor cantilever α (17), likewise, two same variable pressure-sensitive resistors R1 and R2 are located above the pressure-sensitive resistor cantilever β (18). The pressure-sensitive resistors R3 and R4 having fixed resistance are located on the base part of the sensor.

The insulating layer (4) stays above the pressure-sensitive resistor (7) and epitaxial layer cc (3). Contact holes (8) are fabricated to export the pressure-sensitive resistors (7) out of insulating layer (4). Electrodes (9) and metal interconnect lines (10) are located above the insulating layer. The metal interconnect lines connect with pressure-sensitive resistor through the contact holes. The windows (11) are etched and formed out of barrier layer (1). The silicon substrate is etched to form silicon cup (12), the middle part are etched and holed through to form the bilge holes (13). Namely, not only the structure of pressure-sensitive resistor cantilever cc and pressure-sensitive resistor cantilever β are formed, but also the grooves (22), suspended structure (16) and support beams (19) are formed.

The low-dimensional nano-materials (15) are attached between the pressure-sensitive resistor cantilever α (17) and suspended structure (16). The bimetallic strip (14) lies beside the suspended structure, the bimetallic strip (14) component of smaller thermal expansion coefficient is located near the side of suspended structure, the component of bigger thermal expansion coefficient is located away from suspended structure. Heat resistances (20) and thermocouple (21) locate above of bimetallic strip (14).

Figure 3:
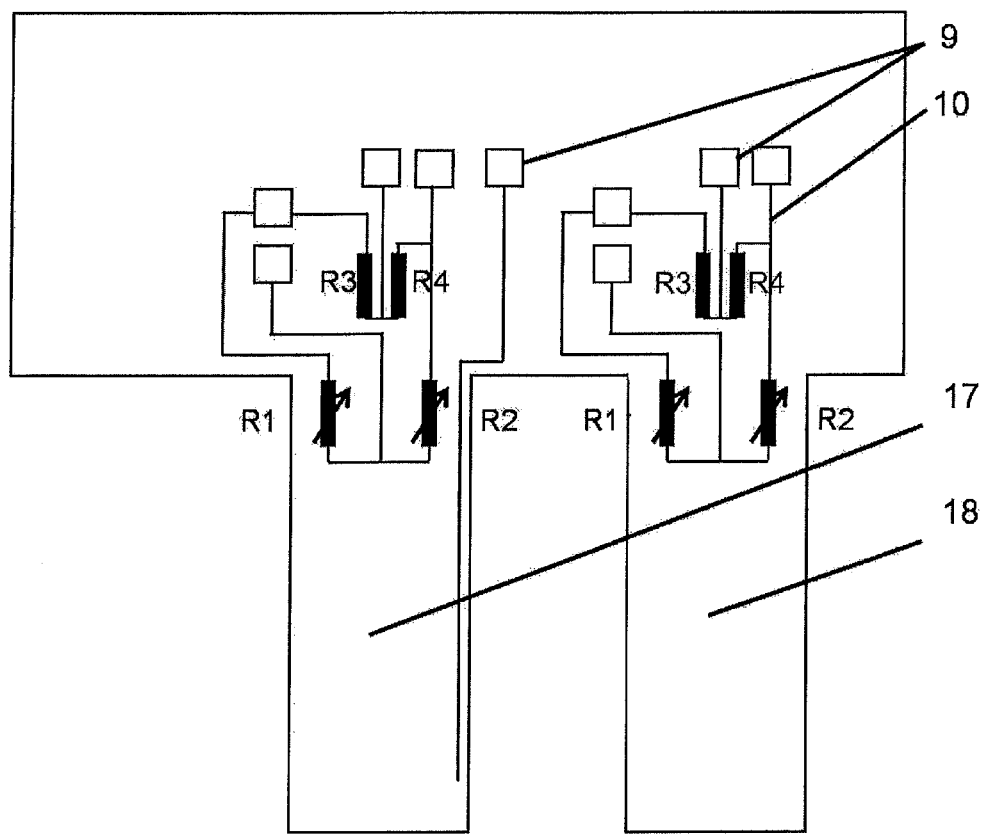
FIG. 3 shows the plan view of the pressure-sensitive resistor cantilevers and Wheatstone bridge circuit.

The following production methods of sensor will describe about quantitative measurement of the electromechanical properties and microstructure of the low-dimensional nano-materials. Further embodiments of the present invention can be implemented by adopting following steps:

1. The specific production and testing methods including: a p-type silicon wafer with thickness of 200 μm, resistivity of 5 Ω.cm and diameter of 2 inches is chosen. Double-sided silicon wafer is polished, the crystal face orientation of the silicon wafer is (100). An epitaxial layer with thickness of 1 um is deposited onto the p-type silicon wafer by the help of low-pressure chemical vapor deposition (LPCVD) technique, with a doping concentration of $3 \times 10^{15}$ cm$^{-2}$ to form n-type epitaxial layer. And then another epitaxial layer with thickness of 1 um is deposited onto the n-type epitaxial layer by the same way, with a doping concentration of $5 \times 10^{15}$ cm$^{-2}$ to form n-type epitaxial layer. Lithography of the p-type epitaxial layer first time to form the eight pressure-sensitive resistors, the shape and resistance of R1, R2, R3, R4 are all the same, the location of eight pressure-sensitive resistors are shown in FIG. 3. Two silicon nitride deposition layers with the same thickness of 0.3 um are deposited above the p-type epitaxial layer and under the p-type silicon layer via plasma enhanced chemical vapor deposition (PECVD) method respectively.

Figure 2:
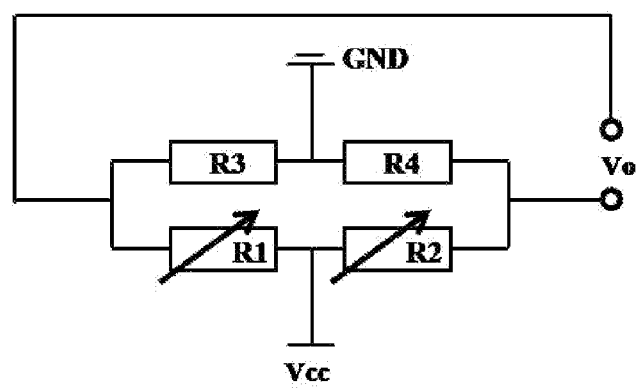
FIG. 2 illustrates sketch map of a Wheatstone bridge circuit of the present invention.

2. The contact holes are formed by lithography of silicon nitride layer above the p-type epitaxial layer second time. After that, by lithography of silicon nitride layer third time, the pattern of electrodes and metal interconnection lines exporting the pressure-sensitive resistors are formed. Finally, a gold layer is sputtered onto the previous pattern to form electrodes and interconnection lines which link up with the eight pressure-sensitive resistors, so that two Wheatstone bridge circuits are formed (FIGS. 2,3).

3. By lithography of silicon nitride layer fourth time from the bottom of p-type silicon wafer, and using reactive ion etching (RIE) method etching silicon nitride layer, windows used for deep etching silicon substrate are formed. Under the condition of 80-100° C. and etching of silicon substrate with mass fraction of 35% potassium hydroxide solution, the wafer is taken out after about 3 hours, and then residual wafer is tested to make sure thickness of 20 um or so, and wafer is cleaned in acetone resolution.

Figure 4:
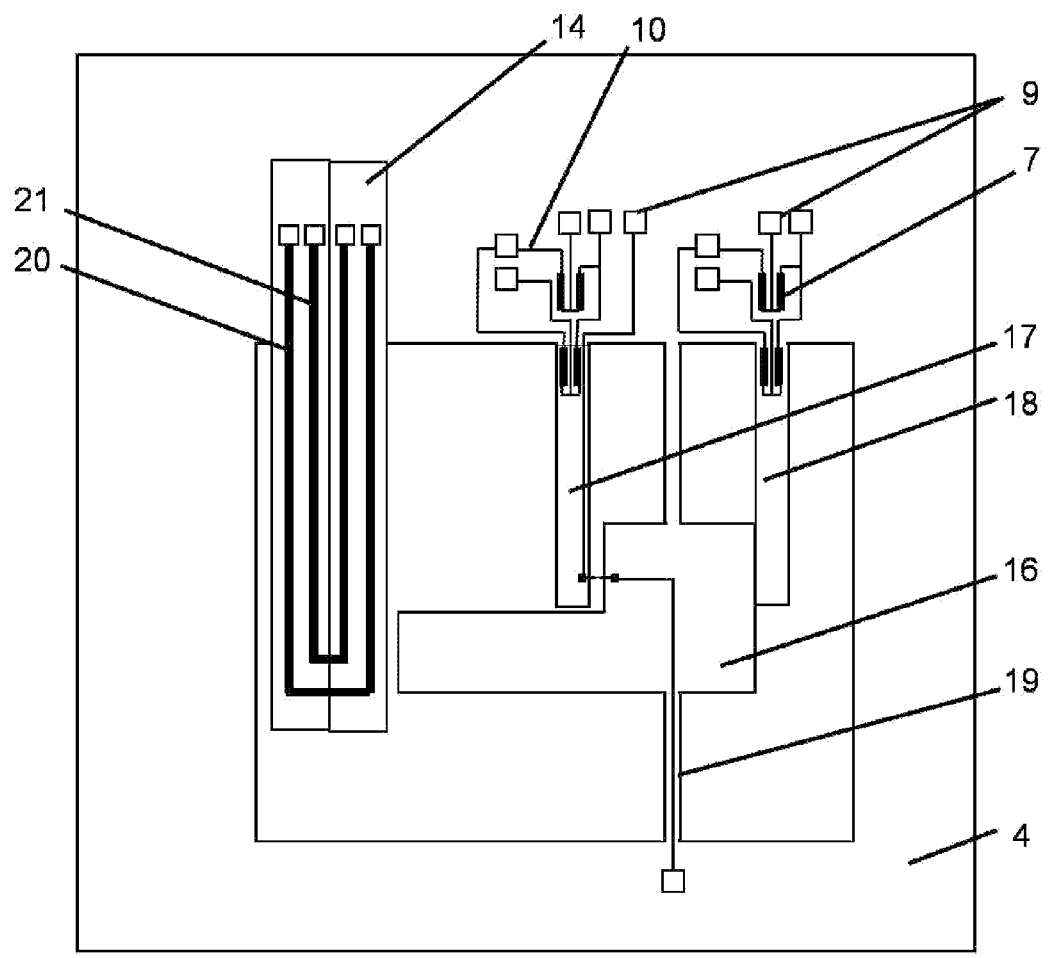
FIG. 4 is the plan view of the sensor of the present invention.

4. Lithography silicon wafer fifth time from the top of p-type is conducted, the residual silicon substrate is etched out by means of RIE. That is, the formation of the required pressure-sensitive resistor cantilever, suspended structure, supporting beams and the groove used for placing bimetallic strip is achieved. The plane view of sensor is shown in FIG. 4 where the length of cantilever is about 500 um, a width is 20 um; the length of supporting beams between silicon substrate and suspended structure is about 500 um, a width is around 10 um; the length and width of the groove are all about 250 um, a depth is 100 um; the horizontal distance between the suspended structure and the pressure-sensitive resistor cantilever cc is about 40. Finally, the wafer is split into an amount of small units which are suitable for setting into TEM sample holder.

5. Bimetallic strip used for driving suspended structure is formed by combination of the alloy $Mn_{72}Ni_{10}Cu_{18}$ with the bigger thermal expansion coefficient and the alloy $Ni_{36}$ with the smaller thermal expansion coefficient. The component of the bimetallic strip with the bigger thermal expansion coefficient is located far away from the suspended structure, and the bimetallic strip with the smaller thermal expansion coefficient is adjacent the suspended structure. After production of bimetallic strip is achieved, the thickness of bimetallic strip attains to 0.1 mm and the width of 0.25 mm, the length of 1.1 mm.

Figure 5:
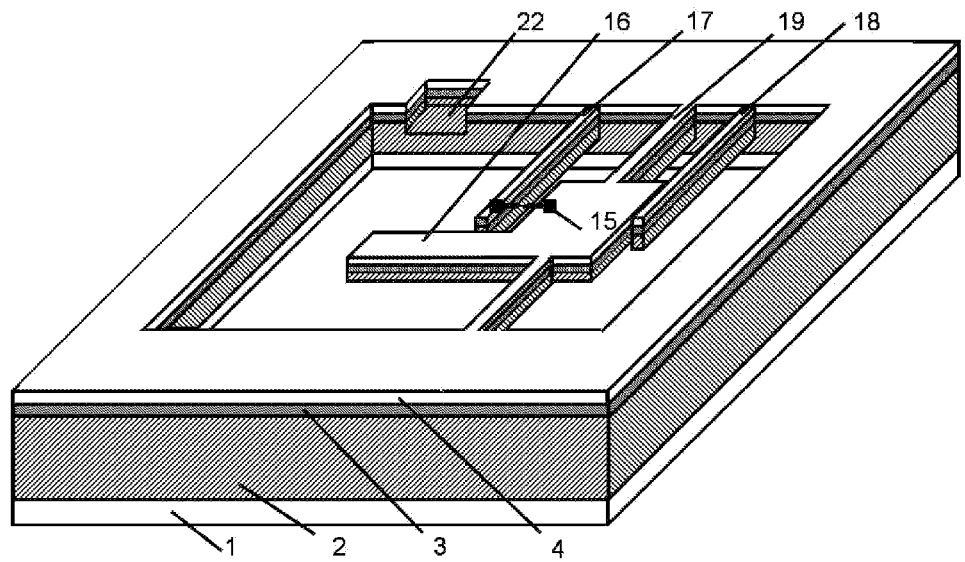
FIG. 5 is the three-dimensional diagram of the sensor before placed the bimetallic strip.
Figure 6:
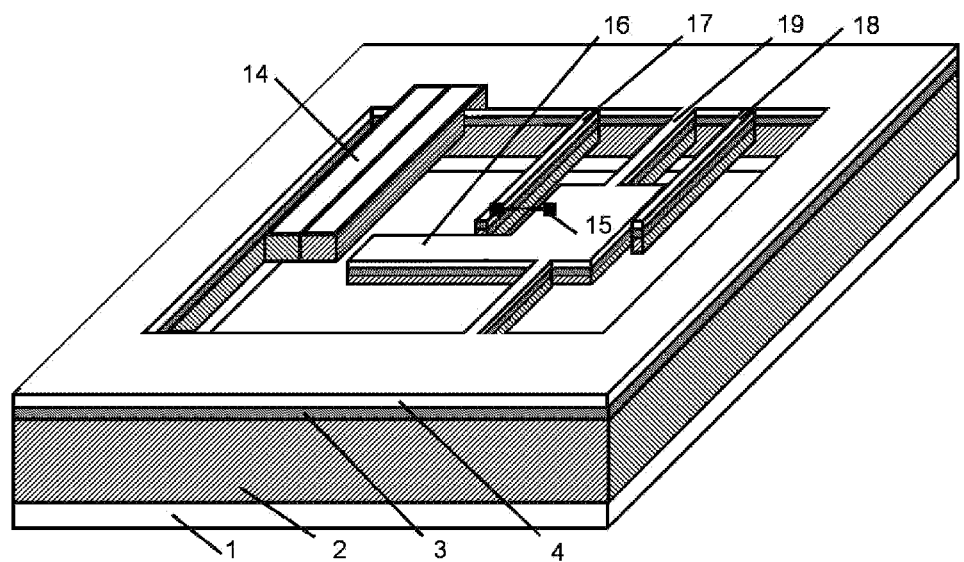
FIG. 6, the three-dimensional diagram of the sensor.

6. The top of the bimetallic strip is covered with the mask block, sputtering a layer of tungsten to form rectangular-shaped heat resistance is conducted, and then the electrodes are leaded from heat resistance. After that, the top of the bimetallic strip is sputtered of patterned iron and copper to form the thermocouple, in order to obtain the temperature of bimetallic strip real-time. The bimetallic strip is adhibited into the pre-etched groove with epoxy resin adhesive. The shape of gold nanobelt is etched and formed out of nanocrystalline gold films by lithography process. After that, gold nanobelt is transferred and fixed to the cantilever beam and suspended structure to build up a complete sensor (FIG. 4-FIG. 6).

The work processes of sensors are described as follows:

The grid with individual gold nanobelt is mounted to TEM sample holder. And then the TEM sample holder is mounted in a transmission electron microscopy. With the grid and electrical TEM holder according to the described above, mechanical and electrical characteristics of individual gold nanobelt can be measured during TEM imaging or before and after TEM imaging which is recorded using films, CCD camera or other means.

The electrodes on the sensor are bonded and leaded out to connect to the transmission electron microscope sample holder with electrification function, and then the electrodes on the bimetallic strip are applied current. When current flow over the heat resistances located on top of bimetallic strip, the heat resistances are heated and heat is transferred to the bimetallic strip. During to the bimetallic strip is heated, bimetallic strip bend towards the side of smaller thermal expansion coefficient, for the volume expansion with the part of bigger thermal expansion coefficient is larger than the part of smaller thermal expansion coefficient. When the bimetallic strip comes into contact with the suspended structure, the suspended structure begins to move. The suspended structure pushes the pressure-sensitive resistor cantilever β (18) to generate bending deformation, while axial-tension is acted on the gold nanobelt (15) to generate tensile deformation. Meanwhile, the gold nanobelt pulls the pressure-sensitive resistor cantilever α (17) to generate bending deformation.

Figure 10:
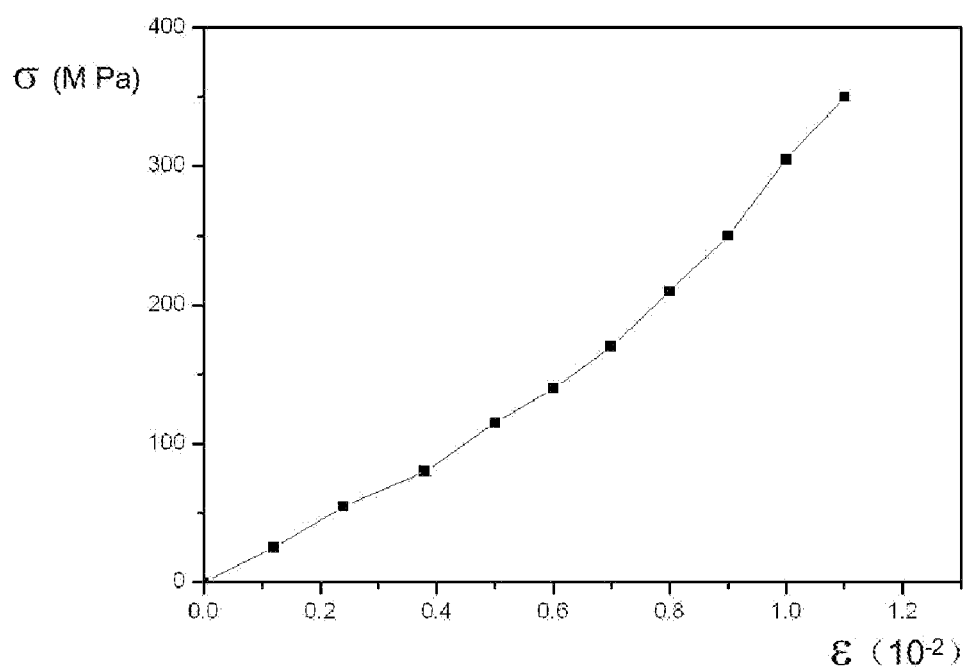
FIG. 10 shows the stress-strain curves of gold nanobelt.

The pressure-sensitive resistors R1 and R2 are located above two cantilever beams, whose resistance changes with the bending deformation of cantilever beams, the resistance changes are transferred into the change of output voltage $V_O$ through the Wheatstone bridge circuit. And then it can be converted to the force size of pressure-sensitive resistor cantilever α (17) $\Delta F_1$ by calculating (For details of the calculation, see T. Chu Duc, J. F. Creemer, and Pasqualina M. Sarro, "Piezoresistive Cantilever Beam for Force Sensing in Two Dimensions", IEEE Sensors Journal, Vol. 7, No. 1, 2007, which is herein incorporated by reference in its entirety.). Similarly, it can be converted to the force size of pressure-sensitive resistor cantilever β (18) $\Delta F_2$ by calculating. Calibration of the stiffness coefficient of pressure-sensitive resistor cantilever α (17) $K_1=(EW_1H_1^3/4L_1^3)$ and the stiffness coefficient of pressure-sensitive resistor cantilever β (18) $K_2=(EW_2H_2^3/4L_2^3)$ is conducted. (Where E is the elastic modulus of the material; L is the total length of the cantilever beam; W and H are the width and thickness of the beam cross-section). Thus the amount of lateral bending deformation about pressure-sensitive resistor cantilever α (17) is $L_1=\Delta F_1/K_1$, the amount of lateral bending deformation about pressure-sensitive resistor cantilever β (18) is $L_2=\Delta F_2/K_2$, then the gold nanobelt (15) producing the quantity of tensile deformation is $\Delta L=L_2-L_1$, namely, we get the strain $\epsilon=\Delta L/L_0$. Applied stress change of gold nanobelt (15) σ is equivalent to the applied force pressure-sensitive resistor cantilever α (17), that is to say $\sigma=\Delta F_1$, so the stress-strain curve of gold nanobelt can be obtained real-time (FIG. 10).

As both ends of gold nanobelt are leaded out of electrodes, while measuring the electrical signal changes about gold nanobelt, the current-voltage (I-V) curve can be obtained real-time under corresponding strain. That is, quantitative study of the correlation of the electromechanical properties and microstructure of the gold nanobelt can be carried out.

Figure 7:
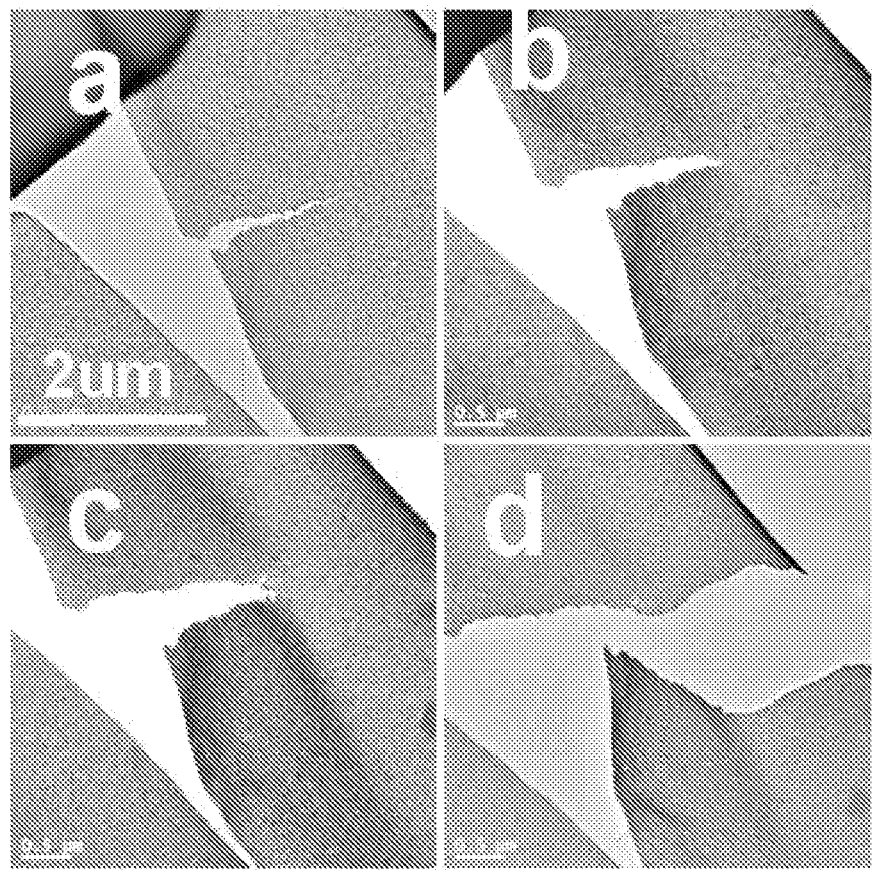
FIGS. 7a-7d show the TEM samples of the gold nanobelt under different strain.
Figure 8:
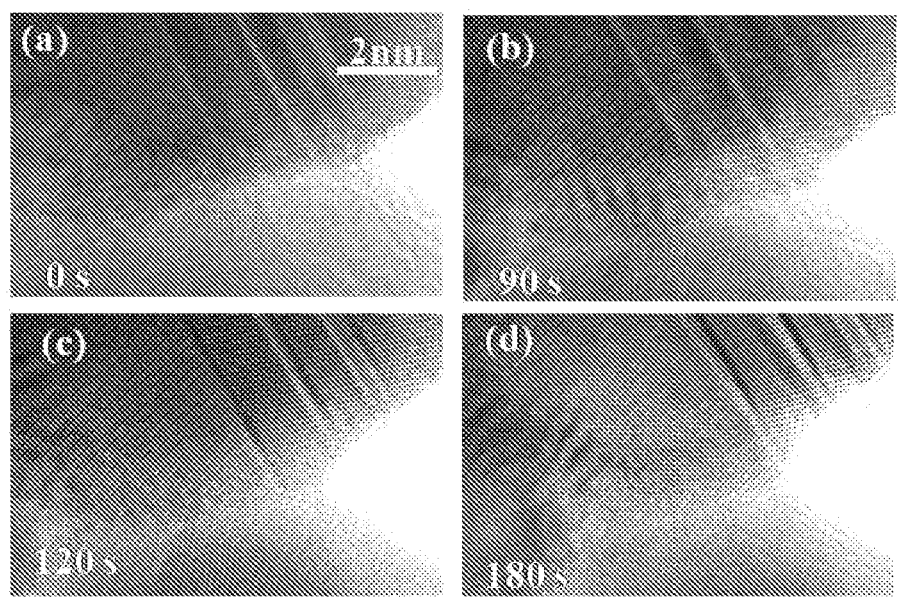
FIGS. 8a-8d show the atomic scale structural changes of the gold nanobelt during the in situ tensile process.
Figure 9:
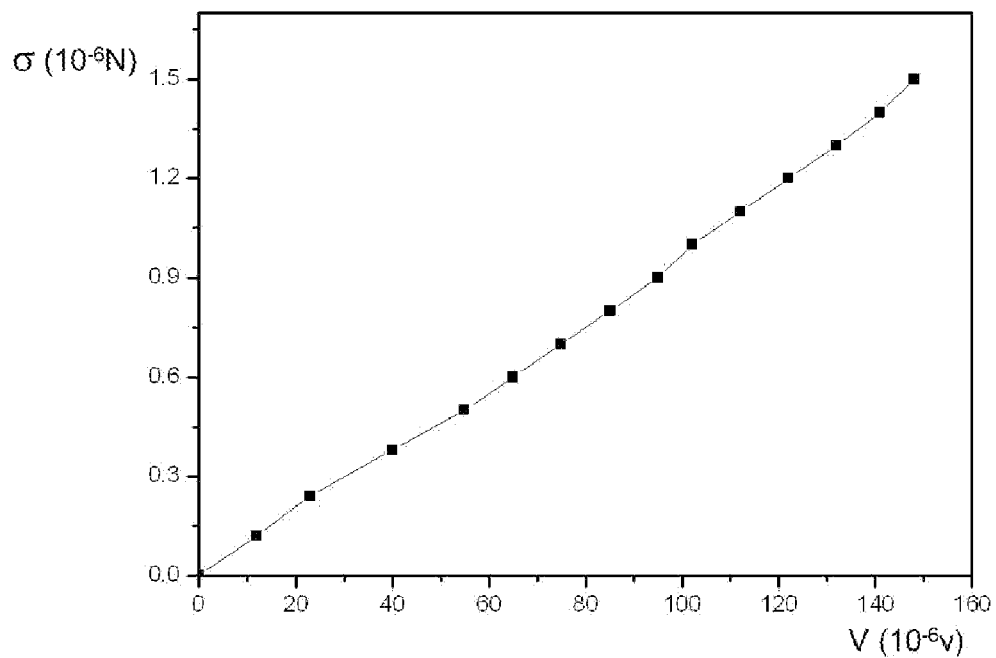
FIG. 9 shows the correlation curve about output voltage signal of Wheatstone bridge and the stress of gold nanobelt.

Meanwhile, the gap between pressure-sensitive resistor cantilever α (17) and suspended structure (16) is about 40 um. When the electron beam penetrates gold nanobelt for imaging, the gold grains inside nanocrystalline gold thin film are turned to low-index zone axis. In situ measurement of microstructure evolutions of the nanobelt at atomic-scale under corresponding strain is conducted, the whole change processes are recorded by high-resolution imaging system (FIGS. 7, 8).

What is claimed is:

1. A sensor for quantitative measurement of electromechanical properties of a nano-material, comprising:
   a hollow structure composed of, from bottom to top, a barrier layer, a silicon substrate, an epitaxial layer α and an insulation layer, wherein a portion of the barrier layer and a portion of the silicon substrate that are located in a middle part of the hollow structure are removed, while a peripheral part of the hollow structure contains the barrier layer, the silicon substrate, the epitaxial layer α and the insulation layer;
   the middle part includes a first pressure-sensitive resistor cantilever, a second pressure-sensitive resistor cantilever and a suspended structure;
   a groove for receiving a bimetallic strip is formed on an upper surface of the peripheral part;
   an upper surface of the bimetallic strip and upper surfaces of the two pressure-sensitive resistor cantilevers and the suspended structure are at the same level;
   the suspended structure is located between the two pressure-sensitive resistor cantilevers, and is not in contact with the first pressure-sensitive resistor cantilever, a side edge of the suspended structure is parallel to a side edge of the first pressure-sensitive resistor cantilever, there is a protruding part bulging from the side edge of the suspended structure, and the protruding part is not in contact with the bimetallic strip, another side edge of the suspended structure is in contact with the second pressure-sensitive resistor cantilever, the suspended structure connects to the peripheral part by support beams;
   a Wheatstone bridge circuit is provided over each pressure-sensitive resistor cantilever and the peripheral part; and
   each Wheatstone bridge circuit, comprising four identical pressure-sensitive resistors, is located between the epitaxial layer α and the insulating layer, two of the four pressure-sensitive resistors located on the peripheral part are used as fixed resistors, another two of the four pressure-sensitive resistors located on top of the pressure-sensitive resistor cantilever are used as variable resistors.

2. A method for producing the sensor according to claim 1, comprising the following steps:
   1), using double-sided polished silicon wafer as the silicon substrate, the epitaxial layer α is deposited above the silicon substrate, then an epitaxial layer β is deposited above the epitaxial layer α;
   2), doping the epitaxial layer β to form a pressure-sensitive resistor layer, conducting a first lithography to the pressure-sensitive resistor layer to form the pressure-sensitive resistors;
   3), depositing an insulation layer onto the pressure-sensitive resistors, while depositing the barrier layer onto a bottom surface of the silicon substrate;
   4), conducting a second lithography to the barrier layer to form a window through the barrier layer, deep etching the windows to expose part of the silicon substrate;
   5), conducting a third lithography to the insulation layer to form contact holes for leading out the pressure-sensitive resistors;
   6), conducting a fourth lithography to the insulation layer to form metal electrodes and metal wires via metal evaporation or sputtering;
   7), conducting a fifth lithography to the insulation layer, etching the middle part of the remaining silicon substrate, the epitaxial layer α and the insulation layer to form the two pressure-sensitive resistor cantilevers, the suspended structure and the support beam, and the groove;
   8), splitting the silicon substrate to form a plurality of units which can be placed into a Transmission Electron Microscopy (TEM); and
   9), producing the bimetallic strip with the size of the bimetallic strip matching with the size of the groove.

* * * * *